United States Patent [19]

Ueda et al.

[11] Patent Number: 5,110,343
[45] Date of Patent: May 5, 1992

[54] CYCLOHEXENONE DERIVATIVES

[75] Inventors: Akiyoshi Ueda; Haruhito Ohishi; Toshio Aihara; Hisao Ishikawa; Kazuyuki Tomida; Hideo Hosaka, all of Tokyo, Japan

[73] Assignee: Nippon Soda Co., Ltd., Tokyo, Japan

[21] Appl. No.: 527,885

[22] Filed: May 24, 1990

Related U.S. Application Data

[63] Continuation-in-part of Ser. No. 274,306, Nov. 21, 1988, abandoned.

[30] Foreign Application Priority Data

Nov. 28, 1987 [JP]  Japan .................. 62-301304

[51] Int. Cl.$^5$ ............... A01N 31/06; C07C 49/453
[52] U.S. Cl. .................. 71/88; 71/98;
71/103; 71/105; 71/123; 71/122; 558/426;
568/29; 568/30; 568/31; 568/42; 568/43;
568/306; 568/329
[58] Field of Search ........ 568/43, 306, 329, 30,
568/31; 71/98, 105, 103, 122, 123, 88; 558/426

[56] References Cited

U.S. PATENT DOCUMENTS

| | | | |
|---|---|---|---|
| 4,209,532 | 6/1980 | Wheeler | 568/43 |
| 4,781,751 | 11/1988 | Chin | 558/415 |
| 4,783,213 | 11/1988 | Lee | 568/329 |
| 4,838,932 | 6/1989 | Knudsen | 71/123 |

OTHER PUBLICATIONS

*Chemical Abstracts*, vol. 85 (1976), Abst. No. 5280f.

Primary Examiner—Mary C. Lee
Assistant Examiner—Jacqueline Haley
Attorney, Agent, or Firm—Joseph C. Mason

[57] ABSTRACT

The invention relates to a herbicidal composition having an inert carrier and an effective amount of a compound having the formula

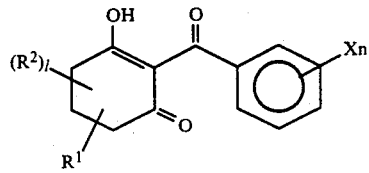

wherein
X is the same or different substituent selected from the group consisting of halogen, nitro, $C_{1-6}$ alkyl, halo $C_{1-6}$ alkyl, $C_{1-6}$ alkoxy, $C_{1-6}$ alkylthio and $C_{1-6}$ alkylsulfonyl;
n is 1, 2, 3 or 4;
$R^1$ is $C_{1-6}$ alkyl which is substituted by cyano, halogen, hydroxy, $C_{1-6}$ alkoxy, $C_{1-6}$ alkylthio, $C_{1-6}$ alkylsulfonyl or tetrahydropyranyloxy; $C_{1-6}$ alkylthio, phenylthio, pyridyl or tetrahydropyranyl;
$R^2$ is $C_{1-6}$ alkyl;
l is 0, 1 or 2.

2 Claims, No Drawings

CYCLOHEXENONE DERIVATIVES

This application is a continuation-in-part of Ser. No. 07/274,306 filed Nov. 21, 1988 now abandoned.

The present invention relates to cyclohexenone derivatives. herbicidal compositions in the form of mixture of such compound(s) with inert carrier(s), and processes for the production of such compounds.

In many cases of agricultural or horticultural cultivation, a lot of kinds and amount of herbicides have come to be used for the weed control in order to save the labors consuming for removing weeds in the fields, however, in some occasion, phytotoxicity of herbicides may injure crops, or herbicides remaining in the field may cause environmental pollution.

Consequently, chemicals possessing the excellent efficacy and the higher safety to mammal have been awaited to be developed.

Cyclohexenone derivatives which are similar to the present invention are described in U.S. Pat. Nos.4,781,751, 4,209,532, 4,838,932, 4,783,213, EP-137963, EP-135191, EP-186118, EP 186119, EP-186120 and Japan Kokai TOKKYO Koho 87-123145.

An object of the present invention is to provide a herbicide which is synthesized advantageously in an industrial scale, gives sure effect at a lower dosage, is highly safety and has good selectivity for crops.

According to the first aspect of the present invention, there is provided a compound having the formula

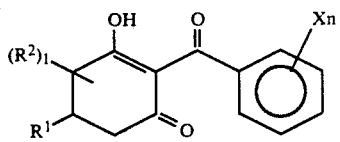

(I)

wherein
X is same or different substitutent selected from the group consisting of halogen, nitro, $C_{1-6}$ alkyl, halo $C_{1-6}$ alkyl, $C_{1-6}$ alkoxy. $C_{1-6}$ alkylthio and $C_{1-6}$ alkylsulfonyl;
n is 1, 2, 3 or 4;
$R^1$ is $C_{1-6}$ alkyl which is substituted by cyano, halogen, hydroxy, $C_{1-6}$ alkoxy, $C_{1-6}$ alkylthio, $C_{1-6}$ alkylsulfonyl or tetrahydropyranyloxy; $C_{1-6}$ alkylthio, phenylthio, pyridyl or tetrahydropyranyl;
$R^2$ is C alkyl;
l is 0, 1 or 2.

According to the second aspect of the present invention, there is provided a herbicidal composition comprising an inert carrier and an effective amount of the compound having the formula (I).

The compounds of the present invention possess superior herbicidal activity against a wide range of varieties of weeds such as Henry crabglass, rice flatsedge, velvetleaf, redroot pigweed, etc. Particularly, the compounds show higher herbicidal activity in post emergence treatment. Some compounds of the present invention have little or a little phytotoxicities to the crops such as corn, wheat, soybeans, etc.

Some compounds also exhibit high selectivity on riceplant and high herbicidal activity against barnyardgrass, smallflower umbrellaplant, arrowhead, Japanese bulrush, etc.

Further, they can be applied for the control of the weeds in orchards, lawn, roadway sides, vacant lots, etc.

According to the third aspect of the present invention, there is provided a process for the preparation of the compound of the formula (I), comprising the step of reaction as illustrated by the following equation.

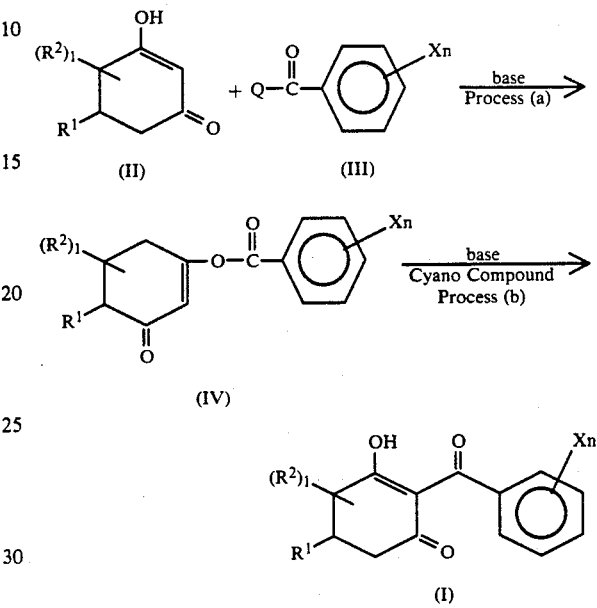

In the above formulae, $R^1$, $R^2$, X, n, and l are as defined aforesaId. and Q is halogen, $C_{1-6}$ alkylcarbonyloxy, $C_{1-6}$ alkoxycarbonyloxy, or

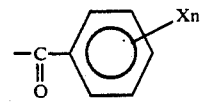

A base used in Process (a) includes an alkali metal hydroxide such as KOH or NaOH, a hydroxide of alkaline earth metal, tri ($C_{1-6}$ alkyl) amine, pyridine, sodium carbonate. and sodium phosphate. A mole of each of compound (II) and compound (III) is used together with a mole or excessive amount of base. A solvent used includes water, methylene chloride, toluene, ethyl acetate, dimethylformamide, THF, dimethoxyethane, and acetonitrile. The reaction mixture is stirred at 0° C. to 50° C. until the reaction is completed. The reaction mixture is treated by an ordinary method.

In Process (b), a mole or compound (IV) is reacted with 1 to 4 moles, preferably 2 moles, of base and an amount from 0.01 to 0.5 moles or more, preferably 0.1 moles, of cyano compound. Any of the bases listed in Process (a) is applicable to this process. A cyano compound used includes potassium cyanide, acetone cyanohydrin and hydrogen cyanide.

The addition of a small amount of phase-transfer catalyst such as crown ether results in the completion of the reaction in a shorter time.

The reaction mixture is stirred until the completion of the rearrangement reaction at a temperature lower than 80° C., preferably 20° C. to 40° C. A solvent used includes 1,2-dichloroethane, toluene, acetonitrile, methylene chloride, ethyl acetate, dimethylformamide. methylisobutylketone, THF, and dimethoxyethane.

The material compound represented by the formula (II) and the compound of the present invention have the following tautomer(s) respectively. The following structural formulae are illustrated with omission of substituents on the cyclohexene ring and benzene ring.

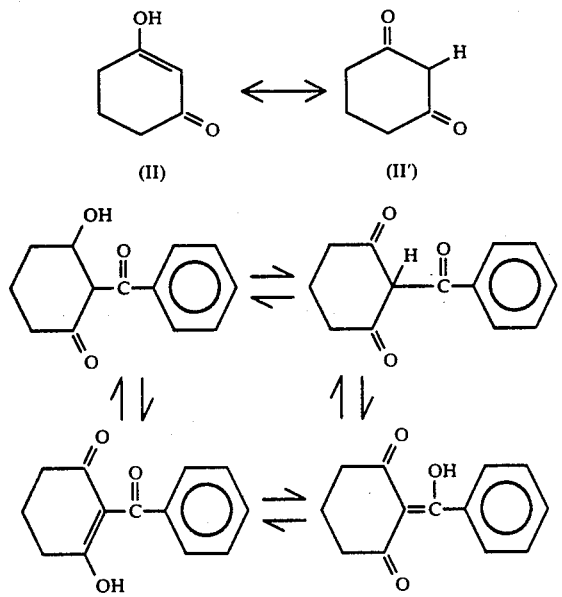

The intended product can be obtained by carrying out a usual after-treatment after the reaction is completed. The structure of the compound of this invention has been determined by means of IR, NMR, MASS spectrum, The following Examples illustrate the invention.

EXAMPLE 1

5-methoxyethyl-2-(2-nitro-4-chlorobenzoly)cyclohexane-1,3-dione (Compound No. 10)

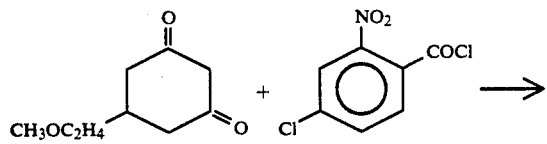

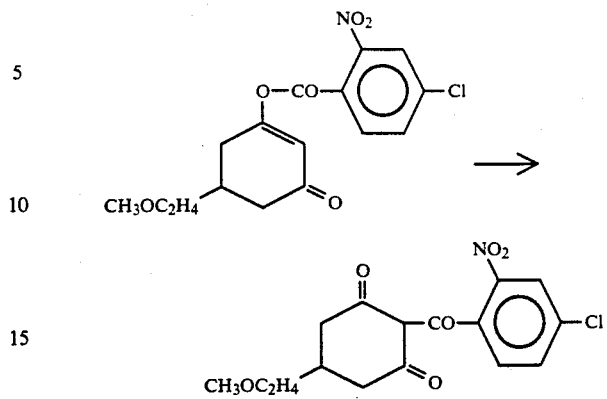

To a solution of 1.7 g (0.01 moles) of 5-methoxyethyl-cyclohexane-1,3-dione and 2.2 g (0.01 moles) of 2-nitro-4 chlorobenzoyl chloride in 20 ml of methylene chloride cooled by ice water bath. 1.1 g (0.0109 moles) of triethylamine was added dropwise while the temperature was maintained below 20° C. After completion of addition, the reaction allowed to proceed at room temperature for 3 hours. The reaction mixture was washed with water, dried over anhydrous magnesium sulfate and concentrated to dryness to give an oily crude product. The residue was dissolved in 20 ml of acetonitrile, and then 1.1 g (0.0109 moles) of triethylamine, 0.06 g (0.00092 moles) of KCN and 0.02 g of 18-crown-6 were added. The reaction mixture was stirred at room temperature for 10 hours. After completion of the reaction, the solvent was removed under reduced pressure. The obtained oily substance was dissolved in 50 ml of ethyl acetate and 10 ml of water. The aqueous layer was made acidic by using diluted hydrochloric acid.

The organic layer was washed with two 10 ml portions of diluted hydrochloric acid, then washed with saturated aqueous sodium chloride, dried over anhydrous magnesium sulfate and concentrated to dryness. The obtained crude product was purified by silica gel column chromatography (eluate: hexane-methylene chloride 1:1 v/v) to give 1.9 g (yield: 53.8%) of the objective product as oil $n^{26}_D 1.5713$).

Inclusive the above, each compound within the scope of the present invention which can be prepared in analogous method(s) is tabulated in Table 1.

TABLE 1

Structure formula

| Compound No. (Old Compound No.) | $R^1$ | $(R^2)_l$ | Xn | Physical properties ( ) mp °C. |
|---|---|---|---|---|
| 1 (66) | —CH$_2$CH$_2$CH$_2$OCH$_3$ | —(l=O) | 2-NO$_2$, 4-SO$_2$CH$_3$ | (126-8) |
| 2 (76) | —CH$_2$CH$_2$OCH$_3$ | " | 2,3-(CH$_3$)$_2$, 4-SO$_2$CH$_3$ | (108-9) |
| 3 (84) | " | " | 2-CH$_3$, 4-SO$_2$C$_3$H$_7^i$ | $n_D^{23}$ 1.5548 |
| 4 (85) | " | " | 2-CH$_3$, 4-SO$_2$CH$_3$ | (107.7) |
| 5 (89) | " | " | 2-Cl, 3-CH$_3$ | oil |
| 6 (91) | " | " | 2,3-Cl$_2$, 4-SO$_2$C$_2$H$_5$ | $n_D^{28}$ 1.5650 |
| 7 | " | " | 2-Cl, 4-OCH$_3$ | oil |

TABLE 1-continued

Structure formula

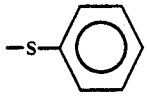

| Compound No. (Old Compound No.) | R¹ | (R²)ₗ | Xn | Physical properties ( ) mp °C. |
|---|---|---|---|---|
| 8 (93) | " | " | 2-Cl, 4-SO₂CH₃ | $n_D^{24.5}$ 1.5141 |
| 9 (98) | " | " | 2,3-Cl₂, 4-SO₂CH₃ | oil |
| 10 (99) | " | " | 2-NO₂, 4-Cl | $n_D^{26}$ 1.5713 |
| 11 (116) | " | " | 2-NO₂, 4-OCH₃ | $n_D^{21.5}$ 1.5813 |
| 12 (119) | " | " | 2-NO₂, 4-SCH₃ | (55-6) |
| 13 (126) | " | " | 2-NO₂, 4-SO₂CH₃ | (135-7) |
| 14 (131) | " | " | 2-NO₂, 4-Cl | (124-5) |
| 15 (154) | —CH₂CN | —(l=O) | 2-NO₂, 4-Cl | (146-8) |
| 16 (156) | —CH₂I | " | " | (129-130) |
| 17 (157) | —CH₂OC₂H₅ | " | " | (84-84.5) |
| 18 (158) | " | " | 2-NO₂, 4-SO₂CH₃ | (115-6) |
| 19 (159) | —CH₂OCH₃ | 4-CH₃ | " | $n_D^{25}$ 1.5685 |
| 20 (163) | " | —(l=O) | 2,3-(CH₃)₂, 4-SO₂CH₃ | $n_D^{25}$ 1.5701 |
| 21 (168) | " | " | 2-NO₂, 4-SO₂CH₃ | (152.5-3) |
| 22 (176) | —CH₂OH | " | 2-NO₂, 4-Cl | (150-2) |
| 23 (177) | —CH₂SC₂H₅ | " | 2-NO₂, 4-CF₃ | (113-5) |
| 24 (207) | " | " | 2-NO₂, 4-Cl | $n_D^{26.5}$ 1.5950 |
| 25 (208) | —CH₂SC₃H₇ⁱ | " | " | $n_D^{22}$ 1.5772 |
| 26 (210) | —CH₂SCH₃ | " | " | (79-80) |
| 27 (212) | —CH₂SO₂CH₃ | " | " | (155-6) |
| 28 (216) | —SCH₃ | 4,4-(CH₃)₂ | " | $n_D^{25}$ 1.5769 |
| 29 (224) |  | " | " | (88-90) |
| 30 (225) | 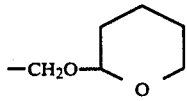 | —(l=O) | " | (155-6) |
| 31 (232) | 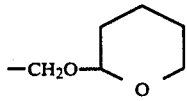 | " | " | $n_D^{24}$ 1.5638 |
| 32 (233) | | " | 2,3(CH₃)₂, 4-SO₂CH₃ | (62-5) |
| 33 (236) | " | " | 2-NO₂, 4-CF₃ | (44-8) |
| (237) | | | | |

TABLE 1-continued

| Compound No. (Old Compound No.) | $R^1$ | Structure formula $(R^2)_l$, $R^1$ with OH and C=O groups, $(R^2)_l$, $X_n$ on phenyl | $X_n$ | Physical properties ( ) mp °C. |
|---|---|---|---|---|
| 34 (238) | tetrahydropyran-4-yl | —(l=O) | 2-NO$_2$, 4-Cl | (43-6) |

As mentioned previously, the compounds possess superior herbicidal activity. The compounds may be applied directly to the soil as pre-emergence treatment or to plant foliage as post-emergence treatment, or they can be mixed intimately with soil. The compounds may be applied to soil or to plant foliage in amount of 1 g or more per 10 are.

A herbicidal composition having a compound of this invention as its active ingredient may be formulated by mixing suitable carriers in a form generally used in agricultural chemicals such as wettable powder, water soluble powder, granule, emulsifiable concentrate and flowable. As solid carriers, talc, white carbon, bentonite, clay, diatomaceous earth or the like may be used. As liquid carriers, water, alcohol, benzene, xylene, kerosene, mineral oil, cyclohexane, cyclohexanone, dimethylformamide or the like may be used. A surface active agent may, if necessary, be added in order to give a homogeneous and stable formulation.

Compounds can also be applied admixed with other chemicals, which are used in agronomic and horticultural management and which are compatible with such compounds. Such chemicals can be, but are not restricted to, the classes of chemical commonly known as fungicides, insecticides, acaricides, herbicides and plant growth regulators. In particular, by mixing it with the other herbicides, its applied dosage and manpower can be decreased and furthermore, the higher effect by synergetic function of both chemicals can be expected.

For admixture of the compound with known herbicides, the use is recommended of benthiocarb, molinate, MY-93 (S-2,2-dimethylbenzil) 1-piperidinecarbothioate) or other carbamate-type herbicides; thiocarbamate-type herbicides; butachlor, pretilachlor or other acid amide-type herbicides; chlormethoxynil, bifenox or other diphenylether-type herbicides; pyrazolate, pyrazoxyfen or other pyrazole type herbicides; chlorsulfuron, sulfometuron or other sulfonylurea-type herbicides; MCP, MCPB or other phenoxy alkane carboxylic acid-type herbicides; diclofopmethyl or other phenoxy propionic acid-type herbicides; fluazifopbutyl or other pyridyloxyphenoxypropionic acid type herbicides; piperophos, dymron, bentazon, oxadiazon, NTN-801 (2-benzothiazole-2-yloxy-N-methyl acetoanilide), naproanilid, HW-52 (4-ethoxy methoxy benzo-2', 3'-dichloroanilide), KNW-242 (1-(3-methylphenyl)-5-phenyl-1H-1,2,4-triazole-3-carboxamide), S-47 (N (α,α-dimethylbenzil)-d-bromotertiary butyl acetoamide, sethoxydim, alloxydim-sodium and other cyclohexanedione-type herbicides. These herbicides in various combinations may also be mixed with a vegetable oil or an oil concentrate.

The concentration of the active ingredient in a herbicidal composition may vary according to type of formulation, and the concentration is, for example, in the range of 5-70 weight percent. preferably 10-30 weight percent, in wettable powder; 3-70 weight percent, preferably 5-20 weight percent, in emulsifiable concentrate; 0.01 30 weight percent, preferably 0.05-10 weight percent, in granule.

A wettable powder, or an emulsifiable concentrate thus produced may be diluted with water to a specified concentration and used as a liquid suspension or a liquid emulsion for treating soils or plant foliage. Further, a granule may be directly used for soil or foliage treatment.

Non-limiting examples of herbicidal composition are illustrated by the following Examples:

EXAMPLE 2

Wettable powder

|  | parts by weight |
|---|---|
| Compound No. 1 | 20 |
| White carbon (Silica) | 20 |
| Diatomaceous earth | 52 |
| Sodium alkylsulfate | 8 |

These are mixed homogeneously and reduced to fine particles to provide a wettable powder containing 20% of active ingredient. In use, it is diluted to a desired concentration with water, and is sprayed as suspension.

EXAMPLE 3

Emulsifiable concentrate

|  | parts by weight |
|---|---|
| Compound No. 6 | 20 |
| Xylene | 55 |
| Dimethylformamide | 15 |
| Polyoxyethylene phenyl ether | 10 |

These are mixed and dissolved to provide an emulsifiable concentrate containing 20% of active ingredient. In use, it is diluted to a desired concentration with water, and sprayed as an emulsion.

EXAMPLE 4

Granule

|  | parts by weight |
|---|---|
| Compound No. 18 | 5 |
| Talc | 40 |
| Clay | 38 |
| Bentonite | 10 |

-continued

| | parts by weight |
|---|---|
| Sodium alkyl sulfate | 7 |

These are mixed homogeneously to provide a granule containing 5% of active ingredient.

The herbicidal effects of compounds are illustrated by the following tests:

TEST 1

Paddy field test

Seeds of barnyardgrass, smallflower umbrellaplant, arrowhead and Japanese bulrush were planted 0.2-0.5 cm in depth in plastic pots (15 cm depth and 14 cm diameter) containing paddy field soil. And then 2 plants of rice seedling (variety: Nihonbare) in 2.5-leaf stage were transplanted from a nursery to each pot. Next day pots were watered 2-3 cm in depth. Immediately granules of each compounds of this invention were applied at the dosage described in the table. The pots were kept in greenhouse.

Three weeks after treatment, the degree of damage of the each plants was observed and evaluated on the scale of value of 0-10, which has the following meanings.

| Index | Degree of damage |
|---|---|
| 0 | 0% |
| 2 | 20-29% |
| 4 | 40-49% |
| 6 | 60-69% |
| 8 | 80-89% |
| 10 | 100 |

Index 1, 3, 5, 7 and 9 mean the intermediate degree between 0 and 2, 2 and 4, 4 and 6, 6 and 8, 8 and 10 respectively.

$$\text{Degree of damage (\%)} = \frac{\text{Fresh weight in untreated plot} - \text{Fresh weight in treated plot}}{\text{Fresh weight in untreated plot}} \times 100$$

The results are shown in Table 2.

TABLE 2

| Compound No. | Application Rate of Active Ingredient (g/10 a) | Degree of Damage (Index) | | | | |
|---|---|---|---|---|---|---|
| | | barn-yard-grass | small-flower umbrella-plant | arrow-head | Japan-ese bulrush | Rice |
| 2 | 25 | 8 | 10 | 10 | 9 | 1 |
| 3 | 25 | 7 | 10 | 10 | 10 | 0 |
| 5 | 25 | 10 | 10 | 10 | 8 | 0 |
| 6 | 25 | 9 | 10 | 10 | 8 | 0 |
| 8 | 25 | 10 | 10 | 10 | 9 | 0 |
| 9 | 25 | 10 | 10 | 10 | 8 | 0 |
| 10 | 25 | 7 | 10 | 10 | 9 | 0 |
| 12 | 25 | 10 | 10 | 10 | 10 | 0 |
| 13 | 25 | 10 | 10 | 10 | 10 | 0 |
| 14 | 25 | 10 | 10 | 10 | 10 | 0 |
| 16 | 25 | 10 | 10 | 10 | 8 | 0 |
| 18 | 25 | 9 | 10 | 10 | 10 | 0 |
| 20 | 25 | 10 | 10 | 10 | 10 | 1 |

TABLE 2-continued

| Compound No. | Application Rate of Active Ingredient (g/10 a) | Degree of Damage (Index) | | | | |
|---|---|---|---|---|---|---|
| | | barn-yard-grass | small-flower umbrella-plant | arrow-head | Japan-ese bulrush | Rice |
| 21 | 25 | 10 | 10 | 10 | 10 | 0 |
| 24 | 25 | 8 | 10 | 10 | 9 | 0 |
| 25 | 25 | 7 | 10 | 10 | 10 | 0 |
| 26 | 25 | 10 | 10 | 8 | 10 | 0 |
| 32 | 25 | 7 | 10 | 10 | 10 | 1 |
| 33 | 25 | 7 | 10 | 10 | 8 | 1 |
| 34 | 25 | 7 | 10 | 10 | 10 | 1 |
| Comparative Compound | | | | | | |
| A | 25 | 6 | 8 | 6 | 5 | 4 |
| B | 25 | 2 | 1 | 0 | 0 | 0 |
| C | 25 | 6 | 6 | 1 | 1 | 4 |
| D | 25 | 7 | 2 | 3 | 2 | 0 |

Comparative Compound A (U.S. Pat. No. 4,781,751)

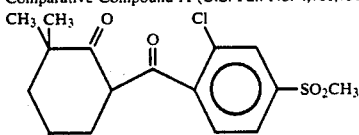

Comparative Compound B (U.S. Pat. No. 4,209,532)

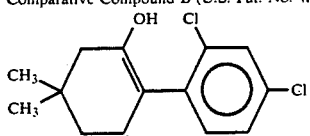

Comparative Compound C (U.S. Pat. No. 4,838,932)

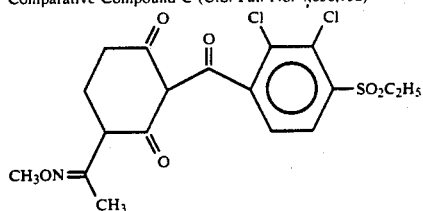

Comparative Compound D (U.S. Pat. No. 4,783,213)

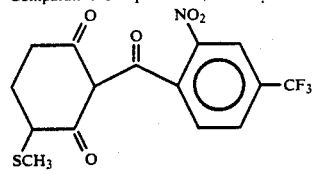

TEST 2

Postemergence treatment test

Seeds of Henry crabgrass, rice flatsedge, velvetleaf, redroot pigweed corn, soybean and wheat were planted in clay pots (12 cm depth and 16 cm diameter) containing clay loam soil and were allowed to grow in greenhouse. When the plants were grown to a 5-10 cm height, aqueous suspensions, prepared by diluting an emulsifiable concentrate with water to specified concentration (500 ppm), were sprayed on the foliage of the plants at a rate of 100 1/10a by using a micro-sprayer. Three weeks after treatment, the degree of damage of the each plants was observed and evaluated on the same scale as in Test 1. The results are shown in Table 3.

TABLE 3

| Compound No. | Application Rate of Active Ingredient (g/10 a) | Degree of Damage (Index) | | | | | | |
|---|---|---|---|---|---|---|---|---|
| | | Henry Crabgrass | rice flatsedge | velvet- leaf | redroot pigweed | corn | soybean | wheat |
| 1 | 50 | 10 | 10 | 10 | 8 | 0 | 7 | 1 |
| 2 | 50 | 10 | 8 | 10 | 10 | 0 | 10 | 9 |
| 4 | 50 | 10 | 10 | 10 | 10 | 0 | 9 | 1 |
| 5 | 50 | 10 | 8 | 10 | 10 | 0 | 7 | 0 |
| 6 | 50 | 10 | 8 | 10 | 10 | 0 | 7 | 0 |
| 7 | 50 | 10 | 10 | 10 | 10 | 0 | 9 | 1 |
| 8 | 50 | 10 | 10 | 10 | 10 | 1 | 9 | 0 |
| 9 | 50 | 10 | 10 | 10 | 10 | 0 | 10 | 0 |
| 11 | 50 | 10 | 10 | 10 | 10 | 6 | 7 | 0 |
| 13 | 50 | 10 | 10 | 10 | 10 | 0 | 7 | 0 |
| 15 | 50 | 10 | 10 | 10 | 10 | 0 | 4 | 6 |
| 16 | 50 | 10 | 10 | 10 | 10 | 0 | 5 | 9 |
| 17 | 50 | 10 | 10 | 10 | 10 | 6 | 1 | 6 |
| 18 | 50 | 10 | 9 | 9 | 9 | 0 | 8 | 1 |
| 19 | 50 | 10 | 10 | 10 | 10 | 0 | 9 | 1 |
| 20 | 50 | 10 | 10 | 10 | 9 | 4 | 10 | 1 |
| 21 | 50 | 10 | 10 | 10 | 10 | 0 | 7 | 1 |
| 22 | 50 | 10 | 10 | 10 | 10 | 0 | 0 | 7 |
| 23 | 50 | 10 | 10 | 10 | 8 | 0 | 2 | 6 |
| 27 | 50 | 10 | 10 | 10 | 10 | 0 | 6 | 4 |
| 28 | 50 | 10 | 10 | 10 | 9 | 0 | 7 | 4 |
| 29 | 50 | 10 | 10 | 10 | 8 | 0 | 6 | 4 |
| 30 | 50 | 9 | 10 | 10 | 10 | 6 | 5 | 1 |
| 31 | 50 | 8 | 9 | 10 | 10 | 4 | 1 | 5 |
| Comparative Compound | | | | | | | | |
| A | 50 | 4 | 8 | 5 | 6 | 4 | 6 | 2 |
| B | 50 | 3 | 4 | 0 | 0 | 0 | 0 | 0 |
| C | 50 | 4 | 8 | 6 | 5 | 5 | 6 | 6 |
| D | 50 | 5 | 4 | 5 | 4 | 4 | 8 | 2 |

*Each Comparative compound is the same as shown in Table 2.

What we claim is:

1. A compound having the formula

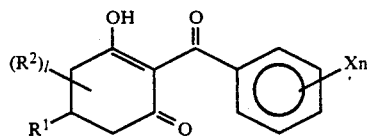

wherein

X is same or different substituent selected from the group consisting of halogen, nitro, $C_{1-6}$ alkyl, halo $C_{1-6}$ alkyl, $C_{1-6}$ alkoxy, $C_{1-6}$ alkylthio and $C_{1-6}$ alkylsulfonyl;

n is 1, 2, 3 or 4

$R^1$ is $C_{1-6}$ alkyl which is substituted by cyano, halogen, hydroxy, $C_{1-6}$ alkoxy, $C_{1-6}$ alkylthio, $C_{1-6}$ alkylsulfonyl or tetrahydropyranyloxy; $C_{1-6}$ alkylthio or phenylthio;

$R^2$ is $C_{1-6}$ alkyl;

l is 0, 1 or 2.

2. A herbicidal composition comprising an inert carrier and an effective amount of a compound of claim 1.

* * * * *